United States Patent [19]

Sugimori et al.

[11] Patent Number: 4,802,985
[45] Date of Patent: Feb. 7, 1989

[54] POROUS WATER-TREATING MATERIAL

[75] Inventors: Shuighi Sugimori; Tomihiko Kawamura, both of Otake, Japan

[73] Assignee: Mitsubishi Rayon Company Ltd., Tokyo, Japan

[21] Appl. No.: 51,235

[22] Filed: May 1, 1987

Related U.S. Application Data

[63] Continuation of Ser. No. 702,637, Feb. 19, 1985, abandoned, which is a continuation-in-part of Ser. No. 563,531, Dec. 20, 1983, abandoned, which is a continuation of Ser. No. 368,249, Apr. 15, 1982, abandoned.

[30] Foreign Application Priority Data

Jun. 19, 1981 [JP] Japan .................. 5995743
Feb. 22, 1984 [JP] Japan .................. 59-30191
Feb. 23, 1984 [JP] Japan .................. 59-31480
Feb. 23, 1984 [JP] Japan .................. 59-31481
Feb. 23, 1984 [JP] Japan .................. 59-31482
Feb. 23, 1984 [JP] Japan .................. 59-31483

[51] Int. Cl.$^4$ .................................... B01D 39/04
[52] U.S. Cl. .................. 210/502.1; 210/504; 210/505
[58] Field of Search .............. 210/502.1, 503-508, 210/680, 693, 924; 502/402, 459

[56] References Cited

U.S. PATENT DOCUMENTS 3,800,945 4/1974 Fowler .................. 210/680
4,332,854 6/1982 Parker .................. 210/924

Primary Examiner—Ivars Cintins
Attorney, Agent, or Firm—Ladas & Parry

[57] ABSTRACT

A porous water-treating material comprising cut porous strads each comprising a resinous matrix material which consists essentially of a thermoplastic polymer material or a mixture thereof with an inorganic particulate material. Each strand having a number of pores connected to each other and an irregularly rugged peripheral surface which has a ratio in diameter of a circumscribed circle to an inscribed circle in any cross-sectional profile from 1.10:1 to 5.00:1 and a ratio of the distance between circumscribed lines to that between inscribed lines in any side projection profile of from 1.10:1 to 3.00:1. The cut porous strands are prepared by melt-extruding a resinous mixture of the resinous matrix material with a blowing agent at a temperature higher than the melting point of the thermoplastic polymer material and the thermally decomposing point of the blowing material so as to cause the strands to have a number of pores and an irregularly rugged peripheral surface thereof.

10 Claims, 1 Drawing Sheet ent Ser. No. 702,637, filed on Feb. 19, 1985, which is a continuation-in-part of Ser. No. 563,531, filed on Dec. 20, 1983, which is a continuation of Ser. No. 368,249, filed on Apr. 15, 1982, all now abandoned.

POROUS WATER-TREATING MATERIAL

CROSS-REFERENCE TO RELATED APPLICATION

This is a continuation of co-pending application Ser. No. 702,637, filed on Feb. 19, 1985, which is a continuation-in-part of Ser. No. 563,531, filed on Dec. 20, 1983, which is a continuation of Ser. No. 368,249, filed on Apr. 15, 1982, all now abandoned.

BACKGROUND OF THE INVENTION

1. Field of the Invention

The present invention relates to a porous water-treating material and a process for producing the same. More particularly, the present invention relates to a water-treating material useful for eliminating organic and/or inorganic substances dispersed, emulsified, and/or dissolved in water in an excellent efficiency and a process for producing the same.

2. Description of the Related Art

Various methods are known for treating waste-water containing organic substances, especially, oily substances. For example, various mechanical water-treating methods are known, such as natural flotation, forced flotation, filtration, and centrifugal gravitational separation methods; electromagnetic methods, for instance, ultrasonic, electrolytic, and electrophoresis separation methods; other physical or chemical methods, for instance, adsorption, absorption, ion-exchange, and coagulation separation methods; and biological separation methods utilizing microorganisms.

Among the above-mentioned methods, a variety of adsorbing materials have been attempted in connection with the absorption method, which features relatively simple and stable operation. However, no adsorbing material has yet been found that is effective for treating finely dispersed and emulsified oily substances. With regard to the adsorbing materials which have now been attempted, for example, the hydrophobic synthetic fibers or fine synthetic resin structures are mainly used for eliminating floating oily substances or coarsely dispersed oily substances in water. Activated carbon in the form of granules is effective to some extent for eliminating finely dispersed oily substances. The activated carbon, however, adsorbs the oily substances in very small amounts and is less effective for eliminating the emulsified oily substances.

In order that the water-treating material exhibit a high capability of eliminating the oily substances from water, it is necessary that the water-treating material have a large specific surface area which results in a high contact efficiency of the water-treating material with the oily substances in water. For example, it is preferable that the water-treating material be of a porous structure.

For the water-treating porous material, attempts have been made to use a resinous matrix material consisting essentially of an organic polymer material alone or a blend of a organic polymer material with an inorganic filler. This type of porous water-treating material is usually prepared by allowing a plate or large mass made of a resinous mixture of the resinous matrix material with a blowing agent to foam and by dividing the resultant porous plate or mass into pieces having a desired size. The dividing step is carried out by a cutting or pulverizing operation.

The pulverizing operation should be followed by a screening operation to collect the porous material particles having the desired size. This, however, complicates the process for producing the water-treating material. Also, the resultant water-treating material particles are distributed over a wide range of size. Therefore, it is difficult to collect particles having the desired size at a high efficiency.

Another disadvantage of the conventional water-treating material is in that it is effective only for eliminating the oily substances floating on the water surface and particles of the oily substances having a relatively large size dispersed in water. That is, a water-treating material effective for eliminating fine particles of the oily substances dispersed or emulsified in water has not yet been formed.

Usually, colloidal particles of the oily substances stably dispersed in water or fine droplet particles of the oily substances or a hydrophobic polymeric substances have negative charges in the surface layer of the particles. The stability of the particles of the oily substances is dependent upon the size of the particles and the amount of the electric charges. Therefore, it is necessary that the water-treating material be capable of neutralizing the negative charges and of the destabilizing the particles of the oily substances. That is, it is preferable that the water-treating material be capable of having charges opposite to those of the particles of the oily substances and of absorbing the oily substance particles therewith. Further, it is preferable that the water treating material include an organic polymer material capable of absorbing or holding the oily substances therewith and, more preferably, that the water-treating material be porous and have a large surface area.

Usually, the process for eliminating the colloidal or fine particles of the oily substances dispersed or emulsified in water is carried out by using a column filled with a water-treating material. In this process, it is preferable that the water-treating material be in the form of grains, granules, or pellets. Also, it is preferable that the distribution in size of the grains be in a narrow range and the grains be capable of precipitating in water.

Furthermore, it is preferable that the small vacant spaces formed between the grains in the water-treating materials be resistant to closure by the solid substances in water so that the pressure of the water flowing through the column filled by the water-treating material can be maintained substantially constant and that, if the small vacant spaces are closed, the solid substances can be easily removed from the water-treating material by washing it with water.

Still furthermore, it is preferable that the water-treating material have a high mechanical strength and hardness.

SUMMARY OF THE INVENTION

An object of the present invention is to provide a water-treating material highly useful for eliminating organic and/or inorganic substances dispersed, emulsified, and/or dissolved in water in an excellent efficiency and a process for producing the same.

Another object of the present invention is to provide a water-treating material effective for clarifying wastewater containing oily substances in the form of fine particles or droplets and a process for producing the same.

The above-mentioned objects can be attained by the porous water-treating material of the present invention, which comprises cut porous strands each comprising a resinous matrix material consisting essentially of at least one member selected from the group consisting of organic thermoplastic polymer materials and mixtures of at least one organic thermoplastic polymer material with at least inorganic particulate material and each having a number of pores formed therein and connected to each other and an irregularly rugged peripheral surface; the irregular ruggedness being to an extent that, in any cross-sectional profile of each cut porous stand, the ratio of the diameter of a circumscribed circle to that of an inscribed circle in the cross-sectional profile is in the range of from 1.10:1 to 5.00:1, and that in any side projection profile of each cut porous stand observed in a radius direction thereof, the ratio of the distance between a pair of circumscribed lines to that between a pair of inscribed lines in the side projection profile, the circumscribed and inscribed lines being parallel to the longitudinal axis of the cut porous strand, is in the range of from 1.10:1 to 3.00:1.

The resinous matrix material may additionally contains a cationic organic cross-linked polymer material.

The porous water-treating material of the present invention can be produced by a process which comprises the steps of: melt-extruding a resinous mixture of a resinous matrix material consisting essentially of at least one member selected from the group consisting of organic thermoplastic polymer materials and mixtures of at least one organic thermoplastic polymer material with at least one inorganic particulate material, with a blowing agent, through a melt-extruding orifice at a temperature higher than both the melting point of the polymer material and the thermally decomposing point of the blowing agent to provide a strand-shaped stream of the resinous mixture while the decomposed blowing agent causes the strand-shaped stream of the resinous mixture to provide a number of pores formed therein and connected to each other and to have an irregularly rugged peripheral surface; solidifying the resultant porous strand-shaped stream; and during or after the solidifying step, cutting the porous strand-shaped stream or the solidified porous strand into a desired length.

The resinous mixture may additionally contains a cationic organic cross-linked polymer material.

DESCRIPTION OF THE PREFERRED EMBODIMENTS

Figure 1:
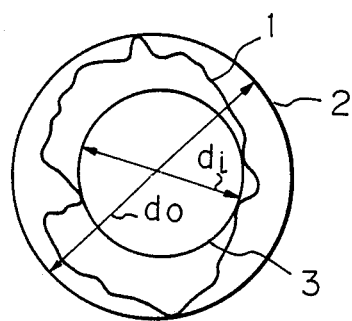
FIG. 1 is a cross-sectional profile of a cut porous strand of the present invention and FIG. 2 is a side projection profile of a cut porous strand of the present invention projected in a radius direction of the porous strand.

The porous water-treating material is composed of a number of cut porous strand having a desired length. The cut porous strands are composed of a resinous matrix material consisting essentially of at least one member selected from organic thermoplastic polymer materials and mixtures of at least one organic thermoplastic polymer material with at least one inorganic particulate material.

The organic thermoplastic polymer material is effective as a component of the cut porous strands for adsorbing oily substances in water.

The inorganic particulate material is effective as a component for enhancing the internal porous structure of the cut porous strands and for increasing the true density of the cut porous strands and, therefore, for enhancing the precipitation property of the cut porous strands in water. Therefore, it is not always required that the inorganic particulate material exhibit a high absorbing activity for the oily substances. It is, however, preferable that the inorganic particulate material be capable of adsorbing the oily substances.

The inorganic particulate material is preferably used in an amount of 75% or less based on the weight of the resinous matrix material. For the purpose of imparting an adequate precipitation property and adsorbing property to the cut porous strands in water, it is preferable that the inorganic particulate material be used in an amount of 20% to 75%, more preferably from 35% to 65%, still more preferably from 40% to 60%, based on the weight of the resinous matrix material.

The organic thermoplastic polymer material usable for the present invention is preferably selected from homopolymers of ethylene, propylene, styrene, butadiene, isoprene, vinyl chloride, vinyl acetate, and acrylonitrile and copolymers containing at least one of the above-mentioned compounds. It is preferable that the organic thermoplastic polymer material consist of an ethylene homopolymer or a copolymer containing, as a principal component, ethylene.

Usually, elastic homopolymers or copolymers such as rubber are not adequate for the present invention, because when they are contained in the resinous matrix material, they cause the internal porous structure and irregularly rugged peripheral surface of the resultant cut porous strands to be unsatisfactory.

The inorganic particulate material usable for the present invention preferably includes at least one member selected from inorganic adsorbing materials and inorganic fillers composed of nickel, zinc, lead, manganese, carbon, oxygen, hydrogen, and/or sulfur. That is, the inorganic particulate material preferably includes at least one member selected from calcium carbonate, calcium silicate, magnesium oxide, magnesium sulfate, barium sulfate, iron oxides, iron hydroxides, hydrate iron oxides, titanium dioxide, titanium hydroxide, hydrate titanium hydroxide, alumina, silica, zinc oxide, manganese dioxide, kaolin clay, montmorillonite, talc, and attapulgite.

In the cut porous strands, the resinous matrix material may contain, as an additional component, an organic cationic polymer material. The organic cationic polymer material is effective for enhancing the water-treating activity of the water-treating material, more particularly, for enhancing the elimination activity for negatively-charged droplets of the oily substances and particles of anionic substances in water. It is preferable that the organic cationic polymer material be a cross-linked polymer.

In the addition of the organic cationic polymer material to the resinous matrix material, the organic cationic polymer material may be directly blended with the resinous matrix material. Otherwise, the organic cationic polymer material may be produced within the resinous matrix material by mixing a cationic compound and a cross-linking compound with the resinous matrix material and by reacting the cationic and cross-linking compounds with each other to prepare a cationic cross-linked polymer material in the resinous matrix material before or during the preparation of the cut porous strands.

The organic cationic cross-linked polymer material is prepared preferably from a cationic component and a cross-linking component.

The cationic component includes at least one cationic compound selected from amino compounds, for example, ethylenediamine, diethylenetriamine, triethylenetetramine, hexamethylenediamine, vinylamine, ethyleneimine and aniline, amino alcohols, for example, N,N-diethylethanolamine, aminoethylethanolamine, N-methyl-N,N-diethanolamine, N,N-diisopropylethanolamine, N,N-dibutylethanolamine, N-methylethanolamine, and triethanol amine; dialkylaminoethyl methacrylate; vinylpyridine; dicyan diamide; vinylimidazoline; and the quaternary ammonium salts of the above-mentioned compounds which are cationized with such a reagent as benzyl chloride, dimethyl sulfate or methyl chloride; or another cationic monomers, polymers or copolymers, for example, 2-hydroxy-3-methacryloxypropyltrimethylammonium halide, a polyester polyamine, polyamide polyamine, a cationic vinyl lactam/acrylamide copolymer, a cyclized polymer of diallylammonium halide, a half-amide obtained by reacting diamine with copolymers of isobutylene and maleic anhydride, a polycondensate of ammonia and epichlorohydrine, quaternary ammoniates obtained by reacting diamine and methyl chloride with a copolymer of styrene and maleic anhydride, polycondensates of alkylene dichloride and alkylene polyamine, polycondensates of aspartic acid and hexamethylene diamine, polycondensates of aniline and formaldehyde, and polymers known as a cationic high molecular coagulating agent such as chitosan. It is also allowable to use sulfonium compounds such as alkyldimethyl sulfonium, and phosphonium compounds such as tetraalkyl phosphoniate.

The cross-linking component may include at least one member selected from epoxy compounds, for example, (poly)ethyleneglycol diglycidyl ether, (poly)-propyleneglycol diglycidyl ether, neopentyglycol diglycidyl ether, (di)glycerol polyglycidyl ether, trimethylolpropane polyglycidyl ether, sorbital polyglycidyl ether, and epichlorohydrine; (meth)acrylates, for example, (poly)ethyleneglycoldi(meth)acrylate, tetrahydrofurfuryl(meth)acrylate, 1,4-butanediol diacrylate, 1,6-hexanodiol diacrylate, neopentylglycol diacrylate, trimethylolpropane triacrylate, and pentaerithritol acrylate; epoxy acrylates, for example, (di)ethyleneglycol diglycidylether dimethacrylate, propyleneglycol diglycidylether diacrylate, glycerolpolyglycidylether polyacrylate, and phthalic acid diglycidylester diacrylate; isocyanates, for example, diphenylmethane diisocyanate, tolylene diisocyanate and hexamethylene diisocyante; hydroxyl group-containing compounds, for example, polyester polyol, polyether polyol, acryl polyol, derivatives of castor oil, derivatives of tall oil and polybutadiene containing hydroxyl groups at the terminals, and prepolymers thereof.

The reaction of the cationic component with the cross-linking component is carried out usually in the presence of a reaction initiator including at least one member selected from hydrogen preoxide, potassium persulfate, sulforous acid, sodium hydrogensulfite, benzoyl peroxide, azobisisobutyl nitryl, amines such as trialkylamine and tetraalkyldiamine, and organic metal compounds such as di-n-butyltin dilaurate. However, the reaction initiators are not always used.

The amount of the cationic polymer material is not limited to any specific range. However, the cationic polymer material is used preferably in an amount of from 0.1% to 20%, more preferably from 0.5% to 13%, based on the weight of the resinous matrix material.

When the resinous matrix material is added with the organic cationic polymer material, the inorganic particulate material preferably includes a silicon-containing inorganic compound.

The silicon-containing inorganic compound is preferably selected from silica, aluminum silicate, magnesium silicate, calcium silicate, talc, attapulgite, montmorillonite, and kaolin clay. Preferably, the silicon-containing inorganic compound is used in an amount of from 1.5% to 75%, more preferably from 3.0% to 75%, based on the weight of the resinous matrix material.

Each cut porous strand of the water-treating material of the present invention has a number of pores formed therein connected to each other and an irregularly rugged peripheral surface.

It is preferable that that cut porous strands have a porosity of from 10% to 60%, more preferably from 20% to 60%.

The porosity is determined in accordance with the equation:

$$\text{Porosity (\%)} = \frac{\rho x}{w} \times 100$$

wherein $\rho$ represents a true density of the porous water-treating material measured by a pycnometer, $w$ represents a dry weight of the porous water-treating material and $x$ represents a volume ($cm^2$) of water (specific gravity = 1.0 $g/cm^3$) impregnated in the fine pores in the porous water-treating material, which volume of water is determined by immersing the water-treating material in water, by eliminating air from the immersed material under vacuum, and by measuring the volume of water contained in the water-treating material.

Figure 2:
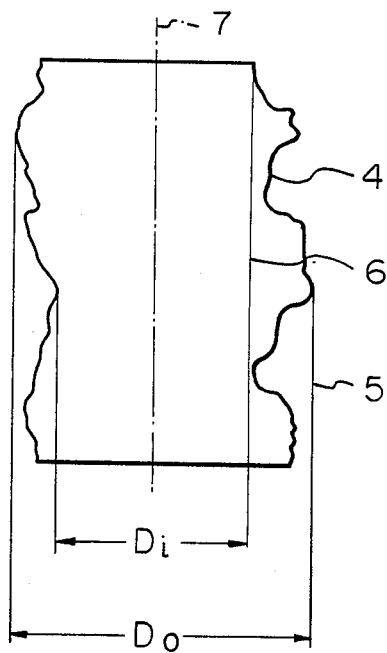

Also, it is necessary that the peripheral surface of the cut porous strands have a number of irregular convexities and concavities, as indicated in FIGS. 1 and 2.

Referring to FIG. 1, a cross-sectional profile 1 of a cut porous strand of the present invention is circumscribed by a circumscribed circle 2 having a diameter $d_o$ and is inscribed by an inscribed circle 3 having a diameter $d_i$. In the present invention, the ratio of the diameter $d_o$ to the diameter $d_i$ must be in the range of from 1.10:1 to 5.00:1, preferably from 1.20:1 to 5.00:1.

Referring to FIG. 2, a side projection profile 4 of a cut porous strand of the present invention projected in a radius direction of the cut strand is circumscribed by a pair of circumscribed lines 5 and is inscribed by a pair of inscribed lines 6. The circumscribed and inscribed lines 5 and 6 are drawn in parallel to the longitudinal axis 7 of the cut strand. The distance between the pair of the circumscribed lines 5 is represented by $D_o$, and the distance between the pair of the inscribed lines 6 is represented by $D_i$. In the present invention, the ratio of the distance $D_o$ to the distance $D_i$ must be in the range of from 1.10:1 to 3.00:1, preferably from 1.15:1 to 3.00:1.

If the diameter ratio $d_o/d_i$ is less than 1.10:1 and/or the distance ratio $D_o/D_i$ is less than 1.10:1, the resultant cut porous strands have an unsatisfactorily poor porous structure and small internal surface area and, thereof, exhibit an unsatisfactorily poor possibility of contacting substances to be eliminated from water and a poor water-treating efficiency. Practically, it is difficult to produce cut porous strands having a diameter ratio $d_o/d_i$ more than 5.00:1 and/or a distance ratio $D_o/D_i$ more than 3.00:1, when the diameter ratio $d_o/d_i$ is in the range of from 1.20:1 to 5.00:1 and/or the distance ratio $D_o/D_i$ is in the range of from 1.15:1 to 3.00:1, the resultant cut porous strands have a remarkably enhanced internal porous structure.

Since the cut porous strands of the present invention have a number of pores formed therein connected to each other and an irregularly rugged peripheral surface, fine particles of substances to be eliminated can contact the surface of the cut porous strands at a high efficiency and, therefore, the cut porous strands of the present invention exhibit an excellent water-clarifying capability.

The cut porous strands may contain additives, for example, stabilizers, emulsifiers, pigments, or dyestuff.

The water-treating material of the present invention can be produced by any process. However, the cut porous strands of the present invention are preferably produced by melt-extruding a resinous mixture of the resinous matrix material as mentioned hereinbefore with a blowing agent through an extruding orifice at a temperature higher than both the melting point of the organic thermoplastic polymer material as mentioned hereinbefore, and the thermally decomposing point of the blowing agent so as to form a stream of the resinous mixture in the form of a strand. The blowing agent is allowed to thermally decompose in the strand-shaped stream. The resultant blowing gas from the blowing agent is released from the strand-shaped stream and, therefore, forms a number of pores in the stream and makes the peripheral surface of the stream irregularly rugged. The resultant porous strand-shaped stream is solidified. During or after the solidifying step, the porous strand-shaped stream or the solidified porous strand is cut into desired lengths.

The blowing agent usable for the process of the present invention preferably includes at least one member selected from organic blowing compounds, for example, azodicarbonamide, benzenesulfonyl hydrazide, toluenesulfonyl hydrazide, and dinitroso-pentamethylenetetramine and inorganic blowing compounds, for example, sodium hydrogen carbonate. The amount of the blowing agent is not limited to any specific value. However, the blowing agent is usually used in an amount of from 0.2% to 5% based on the weight of the resinous matrix material.

The resinous matrix material is mixed with the blowing agent and, optionally, an additive, by using a conventional blender, for example, a V-type blender, drum blender, or a Henschel mixer. The resultant resinous mixture is fed into a melt-extruding apparatus. Usually a conventional melt-extruder, for example, a non-vent type melt-extruder, is used. The melt-extruder has at least one melt-extruding orifice having a desired inside diameter, usually, from 0.5 to 5.0 mm.

The resinous mixture is melted in the melt-extruder at a temperature higher than the melting point of the polymer material and the thermally decomposing point of the blowing agent so as to thermally decompose the blowing agent. In the melt-extruder, the particles of the blowing agent are converted to particles of the resultant decomposition gas compressed and sealed up in the melted resinous matrix material under an elevated pressure. Then, the melt of the resinous mixture is extruded through the orifice to the atmosphere so as to allow particles of the compressed and sealed decomposition gas to freely expand. This phenomenon causes a number of pores to be formed in the resultant stream of the extruded melt of the resinous mixture and to be connected to each other. The expanded decomposition gas ruptures the surface layer portion of the stream of the melt when leaving the stream of the melt. This phenomenon results in the formation of an irregularly rugged peripheral surface of the melt stream.

As mentioned above, the resultant melt stream consisting of the remaining resinous matrix material and having a number of pores and an irregularly rugged peripheral surface is solidified by cooling. During or after the solidifying step, the strand-shaped melt stream of the resinous matrix material or the solidified porous strand is cut into desired lengths. Usually, it is preferably that the length of the cut porous strands be in the range of from 0.3 time to 3.0 times the inside diameter of the melt-extruding orifice.

The degrees of porosity and roughness of the peripheral surface of the cut porous strands are variable depending on the type of the organic thermoplastic polymer material, the content of the inorganic particulate material, the content of the blowing agent, the temperature of a cylinder of the melt-extruder, the inside diameter of the melt-extruding orifice, and the draft pplied to the stand-shaped the stream of the extruded resinous mixture.

If an elastic polymeric material is used as an organic thermoplastic polymer material, if the content of the inorganic particulate material is small, if the content of the blowing agent is small, or if the draft applied to the strand-shaped stream of the extruded resinous mixture is large, the porosity of the resultant cut porous strands and the degree of roughness of the peripheral surface become unsatisfactorily small. Therefore, the type of the resinous matrix material, the amount of the inorganic particulate material and the blowing agent, the melt-extruding temperature, the inside diameter of the orifice, and the draft to be applied to the strand-shaped melt stream should be determined in consideration of the desired degrees of porosity and roughness.

When the solidified porous strand is taken up at a high draft or a high speed, the strand is frequently broken. Therefore, the draft is preferably 3.0 times or less, more preferably, 2.0 times or less. Most preferably, no draft is applied to the melt stream of the extruded resinous mixture.

For the purpose of avoiding undesirable breakage of the porous strands in the melt-extruding and solidifying steps, a plurality of strand-shaped melt streams may be introduced into to a stream of water flowing in the same direction as that of the strand-shaped melt streams and bundled in the water stream. Generally, when the resinous matrix material consists essentially of a thermoplastic polymer material and the resultant strands have a relatively large thickness (diameter), the taking-up operation of the strands can be carried out without difficulty. However, an increase in the content of the inorganic particulate material or a decrease in the thickness of the strands result in increased frequency of breakage of the strands before the solidifying operation is completed. This phenomenon makes the melt-extruding step unstable.

When a plurality of the strand-shaped streams of the melted resinous matrix material having an irregularly rugged peripheral surface are bundled in a water stream, the strand-shaped streams are brought into contact with each other and partially melt-bounded at the convexities on the peripheral surfaces thereof. The partially bonded porous strands can be easily separated from each other by applying a light impact thereto, for example, by cutting the strands by means of a pelletizer.

The use of the water stream is advantageous in that when some strand-shaped streams are broken, the lower-stream portions of the strand-shaped streams are conveyed by the water stream together with the nonbroken strand-shaped streams and the upperstream portions of the strans-shaped streams are also conveyed by the water stream together with the nonbroken strand-shaped streams, are brought into contact with the nonbroken strand-shaped streams, and are partially bounded thereto, and the partially bonded streams are conveyed by the water stream together with the nonbroken streams. That is, all the resultant porous strands are automatically conveyed by the water stream to a taking-up port of the porous strands even if a half number of strands are broken.

The water-treating material of the present invention is highly effective for eliminating oily substances dispersed and/or emulsified in water. Also, colloidal particles, for example, colloidal silica particles having a negative electric charge and anionic substances are easily eliminated by the water-treating material.

In the water-treating material by the present invention containing a cationic cross-linked polymer material, the resinous matrix material can be firmly bounded to the cationic cross-linked polymer material. Therefore, the resultant water-treating material exhibits an excellent durability over a long period of time.

When the water-treating operation is carried out by using a column filled by the water-treating material of the present invention, it is preferably that the cut porous strands be of a diameter of from 1.0 to 2.00 mm and a length of 0.3 to 6.0 mm.

The water-treating material of the present invention is effective for adsorbing oil droplets in water and for coalescing the oil droplets and, therefore, is useful for clarifying various types of oily substance-containing water, for example, wastewater containing cutting oil and rolling oil, wastewater from oil-tank cleaning operations, machine cleaning operations, vehicle cleaning operations, painting factories, and food factories, wastewater drained from compressors, ballast water of oil tankers, bilge water, and wastewater from crude oil drilling operations.

Also, the water-treating material of the present invention is useful for eliminating oily substances from various circulating water for the purpose of recycling.

The present invention will be further explained by way of specific examples, which, however, are representative and do not restrict the scope of the present invention in any way.

EXAMPLES 1 TO 4

In each of Examples 1 to 4, a resinous mixture was prepared by blending polyethylene with barium sulfate or talc and a blowing agent consisting of an azodicarbonamide compound (available under trademark "cellmaik CAP500" and make by Sankyo Kasei) in the amounts as indicated in Table 1. The resultant resinous mixture was fed into a non-vent type melt-extruder provided with a cylinder having an inside diameter of 30 mm and heated at maximum at a temperature of 170° C. and eight circular orifices having an inside diameter of 1.5 mm. The resinous mixture was melted in the cylinder and extruded through the eight orifices to form eight streams of the melt of the resinous mixture in the form of strands. The strand-shaped melt streams were cool-solidified without applying a draft thereto. The resultant solidified porous strands were pelletized to form cut porous strands having a length of about 2 mm.

Side profiles of 10 of the resultant cut porous strands were projected and printed out on photographic printing paper by using a photographic enlarger. From each of the printed side projection profiles, a distance ratio $D_o/D_i$ was obtained. The results are shown in Table 1.

In each of five of the resultant cut porous strands, five cross-sectional profiles were photographed. From each of the resultant 25 cross-sectional profiles, a diameter ratio $d_o/d_i$ was measured. The results are shown in Table 1.

The cut porous strands were charged at a height of 200 mm in a 500 ml measuring cylinder. The filling density of the cut porous strands was as shown in Table 1.

The cut porous strands were charged at a height of 800 mm in a column having an inside diameter of 20 mm to provide a water-treating column.

Testing water containing dispersed oil was passed through the water-treating column at a flow rate of 1.25 l/h (4 m/h) for 200 hours. The testing water was prepared by mixing 1 l of fresh water with 4 g of turbine oil made by Maruzen Oil Co., by means of a mixer for 8 minutes and by diluting the mixture with 40 l of fresh water. The turbidities of the testing water and the treated water were determined by means of a turbidimeter. The results are shown in Table 2. Table 2 also shows the pressure loss of the water-treating column after the water-treating operation for 200 hours.

Table 2 shows that the water-treating columns of Examples 1 to 4 exhibited excellent water-clarifying activity and a very small pressure loss even after the water-treating operation over 200 hours.

Therefore, it is clear that the water-treating materials were very useful for clarifying oil-containing water.

EXAMPLE 5

The same procedures as those described in Example 2 were carried out, except that the melt-extruder was provided with a single orifice having an inside diameter of 3.0 mm, and the length of the resultant cut porous strands was 3.0 mm.

The results are shown in Table 1 and 2.

TABLE 1

| Example No. | Composition of resinous mixture (part by weight) | | | | Extruder | | Cut porous strands | | |
|---|---|---|---|---|---|---|---|---|---|
| | Organic thermoplastic polymer material | | Inorganic particulate material | | Amount of blowing agent * | Inside diameter of orifices (mm) | Distance ratio $D_o/D_i$ | Diameter ratio $d_o/d_i$ | Filling density (g/cm³) |
| | Type | Amount | Type | Amount | | | | | |
| 1 | Polyethylene | 70 | Barium sulfate | 30 | 3.0 | 1.5 | 1.15 to 1.17 | 1.22 to 2.33 | 0.30 |
| 2 | Polyethylene | 50 | Barium sulfate | 50 | 1.5 | 1.5 | 1.34 to 1.92 | 1.38 to 2.94 | 0.44 |

TABLE 1-continued

| Example No. | Composition of resinous mixture (part by weight) | | | | Amount of blowing agent * | Extruder Inside diameter of orifices (mm) | Cut porous strands | | |
|---|---|---|---|---|---|---|---|---|---|
| | Organic thermoplastic polymer material | | Inorganic particulate material | | | | Distance ratio $D_o/D_i$ | Diameter ratio $d_o/d_i$ | Filling density (g/cm$^3$) |
| | Type | Amount | Type | Amount | | | | | |
| 3 | Polyethylene | 30 | Barium sulfate | 70 | 1.5 | 1.5 | 1.27 to 2.35 | 1.45 to 4.12 | 0.57 |
| 4 | Polyethylene | 50 | Talc | 50 | 1.5 | 1.5 | 1.25 to 1.64 | 1.31 to 3.78 | 0.46 |
| 5 | Polyethylene | 50 | Barium sulfate | 50 | 1.5 | 3.0 | 1.31 to 2.10 | 1.62 to 3.27 | 0.41 |

Note:
*Azodicarbonamide compound

TABLE 2

| | Turbidity of treated water (ppm) | | Pressure loss of water-treating column after 200 hours |
|---|---|---|---|
| Example No. | After 10 hours water treatment | After 200 hours water treatment | water treatment (kg/cm$^2$) |
| 1 | 1.8 | 11.3 | 0.01 |
| 2 | 1.1 | 3.8 | 0.01 |
| 3 | 3.6 | 15.8 | 0.01 |
| 4 | 1.7 | 5.8 | 0.01 |
| 5 | | | |

Note:
Turbidity of testing water was 70 to 100 ppm.

TABLE 3

| Example No. | Composition of resinous mixture (part by weight) | | | | | | Amount of blowing agent *2 | Amount of polyethyleneimine | Amount of epoxy compound *3 | Resultant cut porous strands | | |
|---|---|---|---|---|---|---|---|---|---|---|---|---|
| | Organic thermoplastic polymer | | Inorganic particulate material | | | | | | | Distance ratio $D_o/D_i$ | Diameter ratio $d_o/d_i$ | Filling density (g/cm$^3$) |
| | Type | Amount | Type | Amount | Type | Amount | | | | | | |
| 6 | Polyethylene | 50 | silica | 5 | Barium sulfate | 45 | 1.5 | 4.0 | 2.0 | 1.21 to 1.83 | 1.19 to 1.51 | 0.44 |
| 7 | Polyethylene | 50 | Talc | 50 | None | — | 1.5 | 4.0 | 2.0 | 1.25 to 1.64 | 1.31 to 3.78 | 0.46 |
| 8 | EVA *4 | 50 | " | 50 | None | — | 1.5 | 4.0 | 2.0 | 1.15 to 1.41 | 1.15 to 1.32 | 0.47 |
| 9 | Polyethylene | 50 | None | — | Barium sulfate | 50 | 1.5 | 4.0 | 2.0 | 1.34 to 1.92 | 1.38 to 2.94 | 0.45 |
| 10 | Polyethylene | 50 | " | — | Barium sulfate alumina | 45  5 | 1.5 | 4.0 | 2.0 | 1.21 to 1.62 | 1.18 to 1.52 | 0.48 |

Note
*2 . . . Azodicarbonamide compound
*3 . . . Trimethylpropane polyglycidylether
*4 . . . Ethylene - vinyl acetate copolymer containing 18% by weight of copolymerized vinyl acetate

EXAMPLES 6 TO 10

In each of Examples 6 to 10, the same procedures as those described in Example 2 were carried out, except that the resinous mixture used had the composition indicated in Table 3. The resultant cut porous strands exhibited the properties shown in Table 3.

A water-treating column having an inside diameter of 20 mm was filled with the cut porous strands at a height of 800 mm. Testing water was prepared by stirring a mixture of 1 l of water with 4 g of arabian light crude oil in a mixer for 5 minutes, by diluting the mixture with 2 l of water, by leaving the diluted mixture at rest in a drum for 20 hours, and by separating and collecting 100 l of the mixture located in the lower portion of the drum.

The resultant testing water was passed through the water-treating column at a flow rate of 1.25 l/h (4 m/h) for 200 hours.

The results are shown in Table 4.

TABLE 4

| | Turbidity of treated water (ppm) | | |
|---|---|---|---|
| Example No. | After 10 hour water treatment | After 100 hour water treatment | After 200 hour water treatment |
| 6 | 1.5 | 0.7 | 0.6 |
| 7 | 1.8 | 0.6 | 0.4 |
| 8 | 2.2 | 0.9 | 0.8 |
| 9 | 2.6 | 0.8 | 1.0 |
| 10 | 2.4 | 0.8 | 0.7 |

Note:
The turbidity of the testing water was from 10 to 14 ppm.

EXAMPLES 11 TO 13

In each of Examples 11 to 13, the cut porous strands prepared in each of Examples 6 to 8 were respectively subjected to the same water-treating procedures as those described in Examples 6 to 10, except that the testing water was prepared by stirring a mixture of 4 g of turbine oil (produced by Maruzen Oil Co.) and 0.2 g of polyoxyethylenenonylphenylether with 1 l of water by means of a mixer for 8 minutes and by diluting the mixture with 40 l of water and that the water-treating procedures were carried out for 300 hours.

The results are shown in Table 5.

TABLE 5

| Example No. | Type of water treating material used | Turbidity of treated water (ppm) | | | |
|---|---|---|---|---|---|
| | | After 10 hour water treatment | After 100 hour water treatment | After 200 hour water treatment | After 300 hour water treatment |
| 11 | Example 6 | 8.1 | 1.7 | 2.1 | 1.2 |
| 12 | Example 7 | 5.9 | 1.2 | 0.9 | 1.1 |
| 13 | Example 8 | 6.3 | 2.6 | 1.4 | 1.2 |

Note:
Turbidity of the testing water was 90 to 100 ppm.

Table 5 shows that the silicon-containing inorganic compounds, such as silica and talc, in addition to the cationic cross-linked polymer material are highly effective for enhancing the activity of the water-treating material for eliminating emulsified oil.

EXAMPLES 14 TO 17

In each of Example 14 to 17, the same procedures as those described in Examples 1 to 4 were carried out, except that the resinous mixture was of the composition indicated in Table 6, the non-vent type melt-extruder was provided with a cylinder having an inside diameter of 50 mm and 50 circular orifices each having an inside diameter of 1.5 mm and arranged on two concentric circles, and the extruder melt streams of the resinous mixture were introduced and bundled together in a water stream flowing in the same direction as that of the melt streams.

The solidified strands were pelletized at a length of 2 mm. When the melt-extruding procedures were continuously carried out for 30 minutes, the extruded strand-shaped melt streams were broken 3 to 6 times. However, the broken strands were taken up together with the other strands without difficulty. After a cutting operation, it was found that 98% of the resultant cut porous strands were separate from each other. Only a few cut porous strands were fuse-bonded to each other to form lumps consisting of two or more cut porous strands.

The resultant cut porous strands were subjected to the same water-treating procedures as those described in Example 1, except that, in Example 14, the top of the column of the cut porous strands was covered with a metal net because the specific gravity of the cut porous strands is smaller than that of water.

The results are shown in Table 7.

TABLE 7

| Example No. | Turbidity of treated water (ppm) | | Pressure loss of column after 200 hour water treatment (kg/cm$^2$) |
|---|---|---|---|
| | After 10 hour water treatment | After 200 hour water treatment | |
| 14 | 10.7 | 23.1 | 0.01 |
| 15 | 2.3 | 4.8 | 0.01 |
| 16 | 1.6 | 3.3 | 0.01 |
| 17 | 3.3 | 5.0 | 0.01 |

Note:
Turbidity of testing water was 70 to 100 ppm.

Tables 6 and 7 clearly show that hte water-treating materials of the present invention exhibited a high water-clarifying activity even after the water treatment for 200 hours. Also, the pressure loss of the water-treating column was extremely small even after a long period of continuous water treatment.

We claim:

1. A porous water-treating material, in the form of pellets comprising cut porous strands each comprising a resinous matrix material consisting essentially of at least one member selected from the group consisting of organic thermoplastic polymer materials and mixtures of at least one organic thermoplastic polymer material with at least one inorganic particulate material in an amount of from 20% to 75% based on the weight of the resinous matrix material, and at least one organic cationic cross-linked polymer material, and each having a number of pores formed therein and connected to each other and an irregularly rugged peripheral surface; the irregular ruggedness being to an extent such that, in any cross-sectional profile of each cut porous strand, the ratio of the diameter of a circumscribed circle to that of an inscribed circle in the cross-sectional profile is in the range of from 1.10:1 to 5.00:1, that, in any side projection profile of each cut porous strand observed in a radius direciton thereof, the ratio of the distance between a pair of circumscribed lines to that between a pair of inscribed lines in the side projection profile, the

TABLE 6

| Example No. | Composition of resinous mixture (part by weight) | | | | Amount of blowing agent *6 | Resultant cut porous strands | | |
|---|---|---|---|---|---|---|---|---|
| | Organic thermoplastic polymer | | Inorganic particulate material | | | Distance ratio $D_o/D_i$ | Diameter ratio $d_o/d_i$ | Filling density (g/cm$^3$) |
| | Type | Amount | Type | Amount | | | | |
| 14 | Polyethylene | 100 | None | — | 4.0 | 1.13 to 1.16 | 1.20 to 1.89 | 0.82 |
| 15 | Polyethylene | 65 | Barium sulfate | 35 | 2.0 | 1.22 to 1.80 | 1.32 to 2.58 | 0.33 |
| 16 | Polyethylene | 50 | Barium sulfate | 50 | 1.5 | 1.31 to 2.25 | 1.55 to 3.84 | 0.45 |
| 17 | EVA *5 | 50 | Barium sulfate | 50 | 1.5 | 1.21 to 1.78 | 1.34 to 3.46 | 0.44 |

Note:
*5 - Ethylene (82 wt %) - vinyl acetate (18 wt %) copolymer
*6 - Azodicarbonamide compound circumscribed and inscribed lines being parallel to the longitudinal axis of the cut porous strand, is in the range of from 1.10:1 to 3.00:1, and that in the side projection profile of each cut porous strand, an average D of the distance Do between the circumscribed lines and the distance Di between the inscribed lines is in a range of from 0.5 to 5.0 mm, and the length of the profile is in a range of from 0.3 times to 3.0 times the average D.

2. The porous water-treating material as claimed in claim 1, wherein the organic thermoplastic polymer material is selected from the group consisting of homopolymers of ethylene, propylene, styrene, butadiene, isoprene, vinlyl chloride, vinyl acetate, and acrylonitrile and copolymers containing at least one of the above-mentioned compounds.

3. The porous water-treating material as claimed in claim 2, wherein the organic thermoplastic polymer material comprises an ethylene homopolymer or copolymer.

4. The porous water-treating material as claimed in claim 1 wherein in the mixture of the organic polymer material with the inorganic particulate material, the amount of the inorganic particulate material is in the range of from 35% to 65% based on the weight of the resinous matrix material.

5. The porous water-treating material as claimed in claim 1, wherein the cationic organic cross-linked polymer material is in an amount of from 0.1% to 20% based on the weight of the resinous matrix material.

6. The porous water-treating material as claimed in claim 1, wherein the cationic organic cross-linked polymer material comprises a cationic component consisting of at least one member selected from the group consisting of polyalkylene amines, aminoalcohols, aminomethacrylates, pyridine compounds, quinoline compounds, quaternary ammonium salts of the abovementioned amino compounds, dicyandiamide compounds, and imidazole compounds and a cross-linking component consisting of at least one member selected from the groups consisting of epoxy compounds, acrylate compounds, epoxyacrylate compounds, and isocyanate compounds.

7. The porous water-treating material as claimed in claim 1, wherein the resinous matrix material contains an inorganic particulate material comprising a silicon-containing inorganic material consisting of at least one silicone-containing compound selected from the group consisting of silica, aluminum silicate, magnesium silicate, calcium silicate, talc, attapulgite, montmorillonite, and kaolin clay.

8. The porous water-treating material as claimed in claim 7, wherein the silicon-containing inorganic material is in an amount of from 1.5% to 75% based on the weight of the resinous matrix material.

9. The porous water-treating material as claimed in claim 1, wherein the cut porous strands are in a filling density of from 0.2 to 0.9 g/cm$^3$ under no load when they are filled in a water-treating space at a height of 20 cm.

10. The porous water-treating material as claimed in claim 9, wherein the filling density of the cut porous strands is in a range of from 0.3 to 0.7 g/cm$^3$.

* * * * *

UNITED STATES PATENT AND TRADEMARK OFFICE
CERTIFICATE OF CORRECTION

PATENT NO.   : 4,802,985
DATED        : FEBRUARY 7, 1989
INVENTOR(S)  : SHUICHI SUGIMORI ET AL

It is certified that error appears in the above-identified patent and that said Letters Patent is hereby corrected as shown below:

Title Page, Column 30

Line 1, "5995743" should read -- 56-95743--.

Signed and Sealed this

Ninth Day of October, 1990

Attest:

HARRY F. MANBECK, JR.

Attesting Officer

Commissioner of Patents and Trademarks